United States Patent
Khachatrian et al.

(10) Patent No.: US 6,428,783 B1
(45) Date of Patent: *Aug. 6, 2002

(54) BANK OF AUTOCHTHONOUS STRAINS OF MICROORGANISMS AND METHODS OF ITS USE FOR RECOVERY OF INTESTINAL MICROBIOCENOSIS OF THE MEN

(75) Inventors: Robert Khachatrian; Ashot Khachatrian, both of Glendale, CA (US)

(73) Assignee: Medtech Center, Inc., Glendale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/038,621

(22) Filed: Mar. 11, 1998

(51) Int. Cl.⁷ .................................................. C12N 1/20
(52) U.S. Cl. .................. 424/93.3; 424/93.4; 424/93.45; 424/93.44; 424/93.48
(58) Field of Search ............................. 424/93.3, 93.4, 424/93.45, 93.44, 93.48; 435/243, 252.1, 252.4, 252.8, 252.9

(56) References Cited

U.S. PATENT DOCUMENTS 5,443,826 A * 8/1995 Borody ....................... 424/93.3
5,599,795 A * 2/1997 McCann et al. .............. 514/31

* cited by examiner

Primary Examiner—Jean C. Witz
(74) Attorney, Agent, or Firm—Knobbe, Martens, Olson & Bear, LLP

(57) ABSTRACT

The invention concerns microbiology and medicine and may be used for the prophylaxis and treatment of the syndrome of an irritated large intestine in either a human or an animal. The insertion of the samples of the strains of the autochthonous bank into the intestine of a human permits the repair of the broken bacteriocenosis of the intestine due to the use of the entire spectrum of the healthy (normal) microflora of the intestine. The method is as follows: feces samples of a single human are taken during healthy periods beginning 7–15 days after birth and continuing through the course of a lifetime no more than once a year. The autochthonous strains of the normal intestinal microflora are selected from the feces and identified; a culture of each kind of bacteria is separately made on a selective culture medium to a minimum titer of $10^3$–$10^9$ cells/ml; the biomasses of the strains are mixed and stabilized using the special stabilizer; the mixture is divided into separate samples which are conserved and stored during the entire lifetime of the human with periodic testing of the biotiter. During the storage period, a part of the bacterial samples from various periods of life are mixed in equal proportions after biotiter control-this increases the biological activity of the preparation and the acclimatization of bacteria in the human intestine.

The use of the entire spectrum of the normal (healthy) autochthonous microflora of the intestine permits repair of the broken bacteriocenosis of the intestine in the process of treatment of the syndrome of irritated large intestine or to prevent the possible breach of bacteriocenosis during the treatment of the disease.

16 Claims, No Drawings

BANK OF AUTOCHTHONOUS STRAINS OF MICROORGANISMS AND METHODS OF ITS USE FOR RECOVERY OF INTESTINAL MICROBIOCENOSIS OF THE MEN

FIELD OF THE INVENTION

The invention concerns microbiology and medicine and may be used for the prophylaxis and treatment of the syndrome of an irritated large intestine in either a human or an animal.

BACKGROUND OF THE INVENTION

Having the entire spectrum of normal intestine microflora is a necessary link for many metabolic reactions in humans, particularly for eliminating pathogenic microorganisms in the gastrointestinal tract. The microflora participates in the hepatoenteric circulation of the main components of bile; the flora ferments in the distal section of the intestine and inactivates biologically active compounds (biogenic amines), which are discharged together with the digestive juices; the intestinal flora utilizes the non-digested alimentary substances with the formation of amines, organic acids and other compounds which influence the metabolism of the organism.

One of the important functions of the normal intestinal microflora is its participation in the immunological reactivity of macroorganisms. The total reserve of immunoglobins is created as the result of antigenic stimulation by autoflora, most importantly, by the intestinal bacteria.

Methods are known for the prophylaxis of the syndrome of an irritated large intestine in newborns based on the introduction of strains of bifidobacteria from the mother microbial corpus in a dose of $1\times10^8$ to $1\times10^9$ microbial cells into the anal orifice 30–120 minutes after birth (RF Certificate No. 1743607, 1992). This method is effective only when delivery is done by cesarean section. But for the prophylaxis of the syndrome of an irritated large intestine, the entire spectrum of the healthy intestinal microflora is not used, but only a monoculture of bifidobacteria. Besides, the given culture of the bacteria is not adapted to the intestine of the newborn and may not be acclimatized to the intestine, because it is not taken from the newborn intestine (not autostrain). Thus, this method of prophylaxis is not effective enough. When introduced anally, a part of the bacteria may die while passing through the various sections of the gastrointestinal tract.

Methods for creation and use of a complex bacteria preparation for correction of intestinal disbiosis are known, consisting of sampling from the human and making a biomass of autostrains of lactobacteria or *Escherichia coli* with the following combination of microorganisms as a base. Active carbon can serve as a support. The microbial cells are supported on the surface of the active carbon particles in a concentration of $2.1\times10^3$ to $1.0\times10^5$ cells/mm$^2$ of carbon surface area. The active carbon is utilized as a powder with a maximum particle size of 30 microns. The preparation is inserted into the anal orifice of the human three times per every 3–4 days in a dose of 30–100 microbial cells per gram (RF Certificate No. 2017486, 1994). But for the prophylaxis of the syndrome of irritated large intestine, the entire spectrum of the human intestine is not used, but only a monoculture of lactobacteria or Escherichia coli. This fact leads to a decreased efficiency for the prophylaxis procedure. A treatment method for the syndrome of irritated large intestine in humans is known, consisting of the following stages: sampling of feces, dilution of the material to be studied using a sterile physiological solution, its inoculation in various dilutions onto a culture medium, identification, selection of autostrains of normal intestinal microflora (bidifo- and lactobacteria), separate preparation of cultures of each kind of bacteria, mixing the cultures, short-term storage at a temperature of +4 to 7° C., and periodic introduction of the mixture of the given autostrains into the human intestine during the treatment of the disease, but after antibiotic therapy (RF Certificate No. 1286212, 1987).

The main drawback to the known treatment methods for the syndrome of irritated large intestine lies in the use of only the autostrains of bifido- and lactobacteria rather than the entire spectrum of healthy human microflora. Thus, the efficiency of the treatment is decreased. Besides, the selection of autostrains is carried out before antibiotic therapy, in the period when the normal (healthy) microflora of a man is in the "oppressed" state. When introduced anally, a part of the bacteria may die while passing through the gastrointestinal tract: the efficiency of the treatment of the syndrome of irritated large intestine is decreased, and the recovery time is prolonged. We offer a method for creation of a bank of autochthonous strains of microorganisms for the recovery of the intestinal microbiocenosis in humans with a stable treatment-and-prophylactic effect, achieved by simultaneously influencing various links of the broken bacteriocenosis of the human intestine by use of the entire spectrum of the normal (healthy) microflora of the intestine.

SUMMARY OF THE INVENTION

According to the main purpose of the given invention, the following method is offered: feces samples of a single human are taken during healthy periods beginning 7–15 days after birth and continuing through the course of his entire lifetime—periodically, not more often than once a year. The autostrains of the normal intestinal microflora are selected from the feces and identified, a culture of each kind of bacteria is separately made on a selective culture medium to a minimum titer of $10^3$–$10^9$ cells/ml: the biomasses are mixed and a special stabilizer is added; the mixture is divided into separate samples, which are conserved and stored during the entire lifetime of the man with periodic testing of the biotiter.

At the 7th–15th day after birth of a human the formation of the intestinal microflora is complete.

The use of a bank of autochthonous strains of microorganisms including the entire spectrum of the normal intestinal microflora of a human ensures the complex biological influence (when the mixture is introduced into the intestine) directed to the generation of normal microbiocenosis.

In the baby stage (up to 71 year) we select as the normal intestinal microflora: 1. the following kinds of bifidobacteria: Bifidobacterium bifidum, Bifidobacterium brevis, Bifidobacterium infantis; and 2. the following kinds of lactobacteria: Lactobacillus acidophilus, Lactobacillus fermenti.

From the age of 1 year and older we select as the normal intestinal microflora as a rule the bifidobacteria of the types Bifidobacterium longum, Bifidobacterium adolescentis, the lactobacteria of the types Lactobacillus acidophilus, Lactobacillus fermenti, Lactobacillus plantarum, the strains of bacteria *Escherichia coli* and Streptococcus faecium, Streptococcus faecalis, Streptococcus avium, Streptococcus salivarius and Streptococcus bovis.

In order to create a bank of autochthonous strains, it's necessary to provide samples of strains from various periods of life—it ensures a wide spectrum and complex influence.

Each kind of culture is blended together in equal proportion: the loss of biological activity of the various strains in the mixture during the conservation and storage is decreased.

The autostrain culture mixture is stabilized with saccharose-gel or saccharose-starch protection medium at 5–10 mass %. When the concentration of stabilizer decreases, biological activity in the culture decreases during drying and subsequent storage.

The culture samples are preserved through lyophilization.

During the storage period a part of the samples of bacteria autostrains from various periods of life are mixed in equal proportions after biotiter control—this increases the biological activity of the preparation and the acclimatization of the bacteria in the human intestine.

The use of the entire spectrum of the normal (healthy) autochthonous microflora of the intestine permits repair of the broken bacteriocenosis of the intestine in the process of the treatment of the syndrome of irritated large intestine or to prevent the possible breach of bacteriocenosis during the treatment of this disease.

DETAILED DESCRIPTION OF THE PREFERRED EMBODIMENT

In order to form a bank of autochthonous strains of microorganisms, samples of human feces are obtained not earlier than the 7th–15th day after the birth. The selected material is repeatedly diluted by a factor of 10 with sterile physiological solution to a dilution of $10^8$. The material from various solutions is inoculated onto a culture medium of Blaurock, Sabur, Endo, Kalina, MRS-4, or blood agar with polymyxin for determination of the initial levels of *Escherichia coli* and the identification and selection of autostrains of the normal intestinal microflora, from the baby stage, consisting of bidifo- and lactobacteria.

The material from the isolated colonies of lactobacteria (Lactobacillus acidophilus, Lactobacillus fermenti) is cultured on the medium MRS-4, and the isolated colonies of bifidobacteria (Bifidobacterium bifidum, Bifidobacterium brevis, Bifidobacterium infantis) are cultured on the medium of Blaurock. After two days, the cultures are inoculated a second time onto the elective culture medium. After culturing the second time for two days, the colonies of bifidobacteria and lactobacteria are inoculated (separately) onto the above-mentioned mediums of Blaurock and MRS-4 and cultured according to standard methods of production of biomass. For example, the biomass of bifidobacteria (Bifidobacterium bifidum, Bifidobacterium brevis, Bifidobacterium infantis) has a titer of not less than $10^9$ cells/ml, the biomass of lactobacteria (Lactobacillus acidophilus, Lactobacillus fermenti)—not less than $10^9 10^{10}$ cells/ml.

Equal quantities of each kind of the autochthonous strains of the microorganisms are placed into the reactor and mixed. About 5–10 mass% saccharose-gel protection medium (stabilizer) is added to the biomass.

The biomass is then poured into ampullae and dried by standard lyophilization, sealed, and stored at a temperature of not more than $-18°$ C. in order to ensure the activity of the preparation for a long time period, for example, a human lifetime.

Periodically (not less than once a year), the biotiter of one or several samples of the bank is tested by inoculation onto a culture medium specific for the autostrains' mixture and by bacterial counts of each strain. If the biotiter of the stored preparation declines, the entire volume of biomass is activated by culturing on the specific medium until the biotiter reaches the initial level. Thereafter stabilizer is added to the biomass, and storage is continued at a maximum temperature of $-18°$ C.

The second selection of feces samples from the same person is carried out at the age of 1–2 years, and then at the age of 4–5 years and so on throughout the entire lifespan. The processing of the biomass mixture is similar to the above-mentioned method. The difference consists in the changing composition of the normal intestinal microflora as a function of age in the children and adults, as well as in the stabilization of the number of bifidobacteria at the level of $10^8$–$10^{10}$ microbial cells/g of feces. The Bifidobacterium bifidum, Bifidobacterium brevis, Bifidobacterium infantis, which predominate in young children, are replaced with Bifidobacterium longum, Bifidobacterium adolescentis etc., which are common in juveniles and adults.

The material to be studied is repeatedly diluted ten-fold with sterile physiological solution to a level of $10^{-8}$. The material from various stages of dilution is inoculated onto the culture media of Blaurock, Sabur, Endo, Kalina, MRS-4, or blood agar with polymyxin for determination of the initial levels of *Escherichia coli*, lactobacteria, Enterococcus, Staphylococcus and other bacteria of the following types followed by selection of autostrains of the normal intestinal microflora consisting of bifidobacteria, lactobacteria, *Escherichia coli*, milk streptococcus, and Lactobacillus. The isolated colonies of lactobacteria (Lactobacillus acidophilus, Lactobacillus fermenti, Lactobacillus plantarum) are cultured on the medium MRS-4, the isolated colonies of bifidobacteria (Bifidobacterium longum, Bifidobacterium adolescentis) on the medium Blaurock, the isolated colonies of enterococcus (Streptococcus faecium, Streptococcus faecalis, Streptococcus avium, Streptococcus salivarius and Streptococcus bovis) on the medium Kalina, and the isolated colonies of Escherichia coli on blood agar with polymyxin. After culturing for two days, they are inoculated once more onto the corresponding selective culture medium. The colonies are cultured separately on the culture media of Blaurock, MRS-4, Kalina, or blood agar with polymyxin by standard methods to increase the biomass. For example, the biomass of bifidobacteria has a minimum titer of $10^9$ cells/ml, lactobacteria a minimum of $10^9 10^{10}$ cells/ml, *Escherichia coli* a minimum of $10^7$ $10^8$ cells/ml, and Streptococcus faecium a minimum of $10^9$ cells/ml.

Then each type of microorganism is sampled in equal proportions and mixed in the reactor. Saccharose-starch protective medium is added to the biomass of the autostrains at a level of 5–10 mass% of the biomass. The conservation, storage and testing (control) of the autostrains are similar to the technology described above (in the case of newborn). The samples of the mixture are stored for a human lifetime.

Periodically, feces samples are taken from the same man between the ages of 30–45 years and older during the period when he is healthy and in normal intestinal function. The technology of obtaining, preserving, and storing the samples is described above. The samples are stored for the lifetime of this human.

After adjusting the biotiter during storage, the samples of normal intestinal microflora in various periods of the lifetime of the human and prepared in compliance with the above-mentioned technology are mixed in equal proportions. This insures the biological activity of the mixture of newly received samples of autostrains and the acclimatization of the autostrains in the human intestine.

The totality of stored preparations obtained according to the described technology provides the BANK OF AUTOCHTHONOUS STRAINS OF MICROORGANISMS which may be used for the recovery of the intestinal microbiocenosis of the man.

USE OF THE BANK OF AUTOCHTHONOUS STRAINS OF MICROORGANISMS IN THE PRACTICE OF THE TREATMENT OF VARIOUS DISEASES CONNECTED WITH AN IRRITATED LARGE INTESTINE

Diseases based on the syndrome of an irritated large intestine are treated by recovery of the normal intestinal biocenosis with the help of preparations manufactured from the microorganisms of the normal human microflora. These diseases include, for example, allergic dermatoses, the syndrome of chronic fatigue, bronchial asthma etc. There are diseases, for which a complex treatment is needed, taking into consideration the character of the course of the disease, pathogenesis, and possible complications aggravating the base disease. For example, the therapeutic treatment of the above-mentioned diseases may include pharmaceutical agents such as antibiotics, glucocorticoids, or hormones which may cause severe intestinal disorders. In such cases we find it necessary to ensure the physiological sensitization of the human by correcting the microbiocenosis of the large intestine as the therapeutic base of the main illness, thereby increasing the length of the remission period.

The syndrome of irritated large intestine may appear as the base disease, or some severe diseases may be accompanied by it.

1. Syndrome of Irritated Large Intestine

To treat this disease, one ampulla containing a sample of a mixture of autostrains prepared in accordance with the above described technology was opened, and the mixture of autostrains was activated on a differential culture medium in a thermostat for 26 hours at a temperature of +37°±1° C. Thereby the bacteria were acclimatized to the culture conditions. The received culture was used to inoculate a second preparation of the same culture medium in an amount of 5% of the total mass of the culture medium. The received culture medium was incubated at +37°±1° C. until the logarithmic phase of bacteria growth (the 2nd phase), corresponding to the maximal speed of bacteria division, which takes place in the range of 26–38 hours. At this point, there were $10^7$ $10^8$ cells in 1 ml of received solution.

EXAMPLE: Patient B, 42 years. Complaints: water mucous stool (diarrhea), non-regular (once per 2–3 days), meteorism, intestinal flatus. Data of bacteriological analyses: *Escherichia coli*—not more than 1 million, lactobacteria—without growth, bifidobacteria—without growth. No pathogenic microflora.

The ten-day preparation procedure consisted of cleansing enemas with an aqueous solution of manganese and matricaria.

A bacterial culture containing $10^7$–$10^8$ cells per 1 ml was inserted using a catheter in drops into the descending section of the large intestine. The total amount of culture to be inserted is calculated as follows: 1 ml per 1 kg of patient weight per day. The treatment was carried out for 2 days (three times per day). The treatment for an average patient is 60 ml/day for 2 days.

The results of the bacteriogram 1 month after treatment were as follows: *Escherichia coli*—2.60×$10^8$ cells/ml, lactobacteria—$10^9$ cells/ml, bifidobacteria $10^{11}$ cells/ml.

2. Bronchial Asthma

EXAMPLE: Patient S., 38 years. Basic diagnosis: bronchial asthma, infectious-allergic nature. Attacks of asphyxia—6–8 times per a day. Chronic bronchitis, pulmonary emphysema. Accompanying diseases—chronic cholecystopancreatitis, chronic gastritis, obesity of the 3rd stage. Complaints: intestinal disorder, meteorism with diarrhea.

Results of bacteriological examination: *Escherichia coli*—1.2×$10^7$/g, lactobacteria—0, bifidobacteria—0. The activated preparation (bacterial culture) prepared according to the above-mentioned technology was inoculated in drops into the descending section of the large intestine using a catheter. The total amount of the culture inserted was 1 ml per 1 kg of patient weight per day. The daily dose was divided into three doses and was inserted three times per day. The treatment was continued every other day. The treatment lasted three days for a total treatment of 3 ml/kg.

The bacteriogram data one month after treatment were as follows: *Escherichia coli*—2.40×$10^8$ cells/ml, lactobacteria—$10^9$ cells/ml, bifidobacteria—$10^{11}$ cells/ml.

During the following 1.5 years, the symptoms were in remission, with no aggravation of the bronchial asthma.

3. Chronic Fatigue

EXAMPLE: Patient G., 38 years. Complaints: headache, often fatigue, depression, flabbiness, sleepiness. Diagnosis: chronic fatigue. The basic disease was accompanied by serious intestinal disorders: diarrhea pell mell with atonic constipation, pain during defecation.

Results of bacteriological research: *Escherichia coli*—not more than 5.0–10.0 ×$10^7$/ml, lactobacteria—without growth, bifidobacteria—without growth.

The preparation of the bacterial culture and the technology of inoculation was similar to Examples 1 and 2. The total amount of culture to be inserted was 1 ml per 1 kg of patient weight per day, 60 ml/day for the typical patient, inserted in drops 1 time per day and repeated 3 times in 7 days.

Data of bacteriogram 1 month after treatment: *Escherichia coli*—2.2×$10^8$/ml, lactobacteria—$10^9$/ml, bifidobacteria—$10^{11}$/ml.

During the following 1.5 years there were no further intestinal disorders, and the general physical condition was satisfactory. The basic diagnosis was removed 1.5 years after treatment.

4. Allergic Dermatosis

EXAMPLE: Patient D., 48 years. Basic diagnosis—allergic dermatosis with all of the characterized manifestations: static eczema with skin disorders (scabs).

Complaints: undue fatigue, inclination to constipation (1 time in 2–3 days), periodic meteorism. Data of bacteriological analyses: *Escherichia coli*—not more than 8.0×$10^7$/ml lacto—and bifidobacteria—without growth.

The preparation of the bacteria culture and the technology of insertion were similar to those described in Examples 1 and 2. The total amount of culture was inserted in fractions: the first day—15 ml, the second day—30 ml, the third day—60 ml. The course of treatment—3 days (procedures were carried out 1 time per day).

The bacteriogram results one month after treatment were as follows: *Escherichia coli*—2.30×$10^8$/ml, lactobacteria—growth in dilution 109, bifidobacteria—growth in dilution $10^{11}$. There were marked improvements in the skin: in 1 year the scabs on the elbows and hands were almost gone.

What is claimed is:

1. A method for preparing a bank of autochthonous strains of microorganisms for the recovery of the intestinal microbiocenosis of a human comprising:

obtaining a first and a plurality of subsequent feces samples from a selected human periodically during various periods of life of said selected human, wherein said selected human is healthy when the first and the plurality of subsequent feces samples are obtained;

identifying a plurality of species of bacteria in the first and in the plurality of subsequent feces samples, thereby forming a plurality of identified species of bacteria;

culturing a plurality of species of bacteria selected from the plurality of identified species in the first and the plurality of subsequent feces samples, wherein each species is cultured separately on a culture medium suitable for its growth, thereby forming a plurality of cultures;

separately culturing each of said plurality of cultures until the titer of each of said plurality of cultures is in the range of $10^3$–$10^9$ cells per milliliter, thereby forming a plurality of biomasses;

selecting a portion from each of the plurality of biomasses of autochthonous strains of microorganisms;

mixing said portions to form a mixture; and adding a stabilizing composition to said mixture to form a stabilized mixture.

2. The method of claim 1, further comprising:

separating said stabilized mixture into samples; and conserving and storing said samples, thereby forming stored samples.

3. The method of claim 2, further comprising periodically testing the biotiter of said stored samples.

4. The method of claim 1, wherein the first feces sample is obtained in the time period from the 7th to the 15th day after the birth of said selected human.

5. The method of claim 4, wherein the plurality of cultures comprise Bifidobacterium bifidum, Bifidobacterium brevis, Bifidobacterium infantis, Lactobacillus acidophilus, and Lactobacillus fermenti as the normal intestinal microflora.

6. The method of claim 1, wherein the plurality of subsequent feces samples are obtained periodically in the time period from 1 year after the birth of said selected human to the death of said selected human, and wherein each of the subsequent feces samples is obtained at least one year after the previous feces sample was obtained.

7. The method of claim 6, wherein the three or more cultures comprise Bifidobacterium longum, Bifidobacterium adolescentis, Lactobacillus acidophilus, Lactobacillus fermenti, *Lactobacillus plantarum*, strains of *Escherichia coli, Streptococcus salivarius*, and *Streptococcus bocus* as the normal intestinal microflora.

8. The method of claim 1, wherein said portions from each of said plurality of biomasses are selected and mixed in equal amounts.

9. The method of claim 1, wherein said stabilizing composition is saccharose-gel or saccharose-starch protective medium.

10. The method of claim 8, wherein stabilizing composition is added to said mixture in a quantity of 5 to 10% of the mass of said mixture.

11. The method of claim 2, wherein said samples are conserved by lyophilizing.

12. The method of claim 2, further comprising:

activating at least one of said stored samples by incubating said stored sample in a culture medium, thereby forming an activated sample;

selecting a portion of said activated sample;

placing said portion in a second culture medium to form an inoculated sample; and incubating said inoculated sample until logarithmic phase growth occurs.

13. The method of claim 12, wherein the activating step comprises incubation at 37° C.

14. The method of claim 12, wherein inoculating said inoculated sample comprises incubation at 37° C.

15. The method of claim 13, wherein the activating step is conducted for approximately 26 hours.

16. The method of claim 14, wherein inoculating said inoculated sample is conducted for approximately 38 hours.

* * * * *